(12) United States Patent
Roe

(10) Patent No.: US 7,592,740 B2
(45) Date of Patent: Sep. 22, 2009

(54) MINIATURE DRUG DELIVERY PUMP WITH A PIEZOELECTRIC DRIVE SYSTEM

(75) Inventor: Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 89 days.

(21) Appl. No.: 11/936,813

(22) Filed: Nov. 8, 2007

(65) Prior Publication Data

US 2009/0124994 A1 May 14, 2009

(51) Int. Cl.
*H01L 41/08* (2006.01)

(52) U.S. Cl. .................. 310/330; 310/328; 310/331; 310/332; 604/134; 604/151; 604/256

(58) Field of Classification Search ................ 310/328, 310/330–332; 604/31, 134, 151, 256; 259/129.01
See application file for complete search history.

(56) References Cited

U.S. PATENT DOCUMENTS

| | | | |
|---|---|---|---|
| 4,435,667 A | 3/1984 | Kolm et al. | |
| 5,001,382 A | 3/1991 | Umeda et al. | |
| 5,798,600 A * | 8/1998 | Sager et al. | 310/330 |
| 5,942,838 A | 8/1999 | Lee et al. | |
| 6,179,569 B1 | 1/2001 | Kojima et al. | |
| 6,307,304 B1 * | 10/2001 | Yorio et al. | 310/339 |
| 6,417,601 B1 * | 7/2002 | Kim | 310/333 |
| 6,661,160 B2 | 12/2003 | Kim | |
| 6,787,972 B2 | 9/2004 | Kim et al. | |
| 6,806,621 B2 * | 10/2004 | Heim et al. | 310/328 |
| 6,853,507 B2 | 2/2005 | Ryu et al. | |
| 7,071,596 B2 * | 7/2006 | Krill | 310/328 |
| 7,221,534 B2 | 5/2007 | Anderson et al. | |
| 2002/0005681 A1 * | 1/2002 | Koopmann et al. | 310/328 |
| 2005/0285479 A1 * | 12/2005 | Machida | 310/328 |

FOREIGN PATENT DOCUMENTS

JP 61-35175 * 2/1986

* cited by examiner

*Primary Examiner*—Thomas M Dougherty
(74) *Attorney, Agent, or Firm*—Dinsmore & Shohl LLP

(57) ABSTRACT

A drug delivery pump which uses a piezoelectric drive system to advance a small syringe piston to deliver a liquid drug and a method thereof are disclosed. The present invention has a cost and size advantage compared to traditional pumps and is a very compact and potentially disposable pump device design.

21 Claims, 4 Drawing Sheets

MINIATURE DRUG DELIVERY PUMP WITH A PIEZOELECTRIC DRIVE SYSTEM

FIELD OF THE INVENTION

The present invention is generally related to miniature drug delivery pumps, and in particular to a miniature drug delivery pump with a piezoelectric drive system having a unidirectional clutch.

BACKGROUND OF THE INVENTION

Typically miniature drug delivery pumps use an electric motor and a system of many gears to reduce the high speed motors down to a slower speed. The slower speed provides the precision needed to control the very small doses of a liquid drug being delivered by means of an advancing lead screw and nut moving the syringe piston. Due to the above performance requirements, such miniature drug delivery pump use an expensive high quality electric motor and the associated high quality gears, therefore making such pumps expensive and generally not disposable in nature.

SUMMARY OF THE INVENTION

It is against the above background that the present invention provides a drug delivery pump which uses a piezoelectric drive system to advance a small syringe piston to deliver a liquid drug and a method thereof. The present invention has a cost and size advantage compared to traditional pumps and is a very compact and potentially disposable pump device design.

In one embodiment, a drive system is disclosed, and comprises a lead screw having a rotational axis, a shaft extending along the rotational axis and configured to rotate the lead screw about the rotational axis, and a piezoelectric bender configured to produce reciprocating lateral motion adjacent the rotational axis. A clutch is coupled to the shaft and configured to rotate about the rotational axis. The drive system also includes a wheel mounted to the clutch and operably connected to the piezoelectric bender, wherein the wheel is arranged to convert the reciprocating lateral motion of the piezoelectric bender into reciprocating rotary motion about the rotational axis which turns the clutch bi-directionally, and wherein the clutch in only one direction turns the shaft which advances the lead screw.

In another embodiment, a method for dispensing a liquid drug from a drug container having a piston is disclosed. The method comprises providing a lead screw connected to the piston of the drug container, wherein the lead screw has a rotational axis. The method also includes providing a shaft extending along the rotational axis and configured to rotate the lead screw about the rotational axis, providing a piezoelectric bender configured to produce reciprocating lateral motion adjacent the rotational axis, and providing a clutch coupled to the shaft and configured to rotate about the rotational axis. The method further includes providing a wheel mounted to the clutch and operably connected to the piezoelectric bender, wherein the wheel converts the reciprocating lateral motion of the piezoelectric bender into reciprocating rotary motion about the rotational axis turning the clutch bi-directionally, and wherein the clutch in only one direction turns the shaft which advances the lead screw and the piston dispensing the liquid drug from the drug container.

These and other features and advantages of the invention will be more fully understood from the following description of various embodiments of the invention taken together with the accompanying drawings.

BRIEF DESCRIPTION OF THE DRAWINGS

The following detailed description of the various embodiments of the present invention can be best understood when read in conjunction with the following drawings, where like structure is indicated with like reference numerals and in which.

DETAILED DESCRIPTION

It is against the above background that the present invention provides a miniature drug delivery pump which uses a piezoelectric drive system to advance a syringe piston to deliver a liquid drug and a method thereof. The present invention has a cost and size advantage compared to traditional miniature drug delivery pumps and is a very compact and potentially disposable pump device design due to cost.

In the following description of the embodiments of the invention, skilled artisans appreciate that elements in the figures are illustrated for simplicity and clarity and have not necessarily been drawn to scale. For example, the dimensions of some of the elements in the figures may be exaggerated relative to other elements to help to improve understanding of embodiment(s) of the present invention. Accordingly, the drawings are merely schematic representations, intending to depict only typical embodiments of the invention, and therefore should not be considered as limiting the scope of the invention. The invention will be described with additional specificity and detail through the accompanying drawings. The description of the invention may contain, for example, such descriptive terms as up, down top, bottom, right or left. These terms are meant to provide a general orientation of the parts of the invention and are not meant to be limiting as to the scope of the invention.

Figure 1:
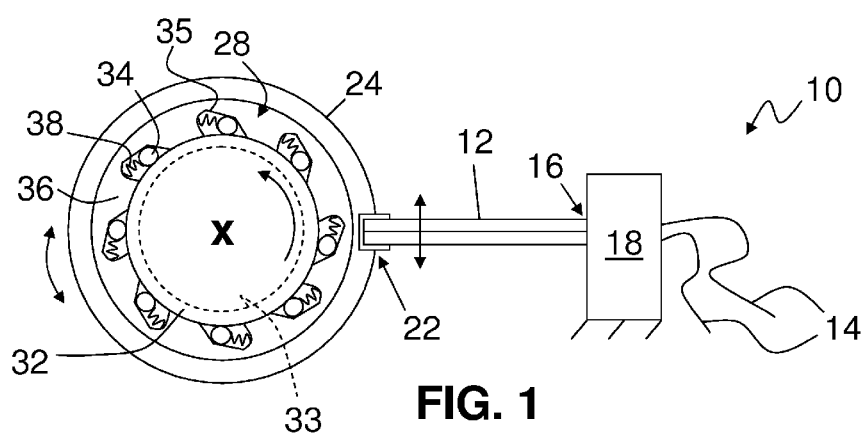
FIG. 1 is a side end view of one embodiment of a piezoelectric drive system having a unidirectional clutch suitable for use with a miniature drug delivery pump according to the present invention.
Figure 2:
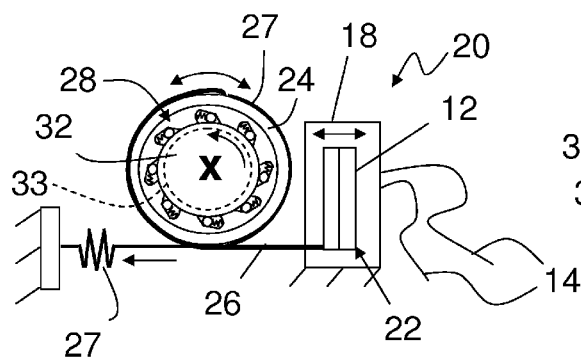
FIG. 2 is a side end view of another embodiment of a piezoelectric drive system having a unidirectional clutch suitable for use with a miniature drug delivery pump according to the present invention.
Figure 3:
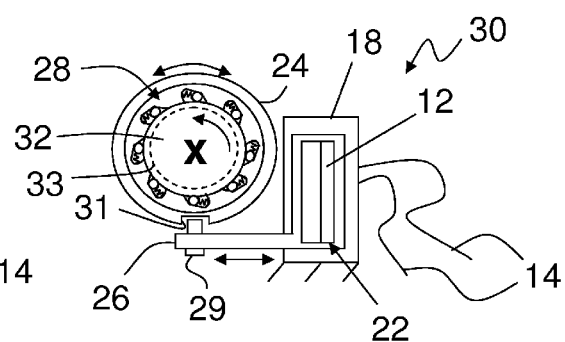
FIG. 3 is a side end view of still another embodiment of a piezoelectric drive system having a unidirectional clutch suitable for use with a miniature drug delivery pump according to the present invention.

Referring now to FIGS. 1-3, various illustrative embodiments of a piezoelectric drive system according to the present invention are shown, and generally indicated by symbols 10, 20, and 30. All embodiments of the drive system 10, 20, and 30 are reciprocating in design which turns lateral motion into rotary motion.

The present invention uses a simple back and forth flexing motion (i.e., lateral motion) of a piezoelectric bender 12. The piezoelectric bender 12 may comprise any type of piezoelectric crystal. One example of the piezoelectric bender 12 is a laminate piezoelectric crystal stack, which is driven by a voltage applied via wires 14 through its range of motion. In that case, voltage changes across the piezoelectric bender 12 cause expansion or contraction of piezoelectric crystals in the stack to induce the desired lateral motion. Another example of the piezoelectric bender 12 is a "bi-morph" piezoelectric crystal structure, which comprises flat piezoelectric crystals that are glued together. A bi-morph piezoelectric crystal structure bends in response to voltage changes applied across the crystals because the different layers expand or contract differently. In the following description, it is assumed that piezoelectric bender 12 comprises a laminate piezoelectric crystal stack. However, the invention is not limited in this respect and may find application with "bi-morph" piezoelectric crystal structures or other piezoelectric crystal elements.

In the illustrated embodiments of FIGS. 1-3, the piezoelectric bender 12 is fixed at one end 16 to a support 18, which is best shown by FIG. 1. The other end 22 of the piezoelectric bender 12 is allowed to move laterally but is operably connected to a wheel 24 and causes the wheel 24 to oscillate on an axis of rotation, indicated by symbol "X", upon application of the voltage via wires 14. It is to be appreciated that in the embodiment of the drive system 10 illustrated by FIG. 1, the piezoelectric bender 12 is orientated perpendicular to the axis of rotation X of the wheel 24. In this embodiment, the end 22 of the piezoelectric bender 12 is coupled directly to the wheel 24. In the embodiments of the other drive systems 20 and 30 illustrated by FIGS. 2 and 3, respectively, the piezoelectric bender 12 is orientated parallel to the axis of rotation X of the wheel 24 and operably connected to the wheel 24 via an extension 26. In the embodiment of FIG. 2, the extension 26 is a wire of a suitable flexible material such as a metal, polymer, fiber, or combination thereof, that is connected at a first end to the end 22 of the piezoelectric bender 12, wrapped partially or fully around the wheel 24, and connected at a second end thereto. In this embodiment, the extension 26 has very little, if any, elongation as the wire is needed to pull on the wheel 24 in order to transfer the lateral movements of the piezoelectric bender 12 to the wheel 24. A return spring 27 may also be provided to maintain the wire (extension 26) under tension around the wheel and to provide the return force needed to slip the clutch in the non-drive direction 24. Both the extension 26 and return spring may be fixed to the wheel 24 via gluing, pinning, or any other suitable joining means.

In the embodiment of FIG. 3, the extension 26 is a material such as a metal, polymer, or combination thereof, which has a first portion surrounding the end 22 of the piezoelectric bender 12 and a second portion provided a distance from the first portion which is coupled to the wheel 24. In this embodiment, the extension 26 is fixed to the wheel 24 via a pin 29 that is fitted into a slot or recess 31 provided in the wheel 24.

As shown by FIGS. 1-3, provided inside the wheel 24 is a unidirectional ratchet or clutch 28 such as, for example, a one-way roller clutch or Sprague clutch. The wheel 24 and clutch 28 may be fixed together via gluing, pinning, pressing, fitting, or any other suitable joining means. As the back and forth oscillation of the wheel 24 occurs, the clutch 28 will alternately slips in one direction (e.g., clockwise) and then grabs in the opposite direction (e.g., counter-clockwise) for each lateral cycle of the piezoelectric bender 12 i.e., the up and down motion of the piezoelectric bender 12 in references to the embodiment of FIG. 1, or side to side motion of the piezoelectric bender 12 in reference to the embodiments of FIGS. 2-3. As the clutch 28 turn in the non-slip direction, a shaft 32 which runs thru the clutch 28 also turns in the non-slip direction. In all the embodiments, the shaft 32 is a hollow tube having a center cavity, which is represented by a dashed line that is indicated by symbol 33.

An example of a unidirectional clutch 28 which may be used is shown in detail by FIG. 1. In this example, the unidirectional clutch 28 is a one-way roller clutch; however, the invention is not limited in this respect and may find application with other unidirectional clutches. As the wheel 24 rotates in the counter-clockwise direction, clutch rollers 34 jam between the shaft 32 and the clutch body 36, locking them together. This allows the angular displacement of the wheel 24 to be transmitted to the shaft 32. As the wheel 24 and clutch 28 rotate in the opposite (clockwise) direction, springs 38 between the clutch rollers 34 and clutch body 36 are compressed by the rollers, the rollers 34 slip, and the wheel 24 and clutch body 36 rotate freely about the shaft 32, so that no clockwise angular displacement of the wheel 24 is transmitted to the shaft 32. Thus, in this embodiment, the roller clutch 28 transmits angular displacement of the wheel 24 to the shaft 32 only if the wheel 24 and clutch 28 move in the counter-clockwise direction when the rollers 34 are wedged between their respective tilted slope pockets 35 of the clutch body 36 and outer surface of the shaft 32.

Figure 4:
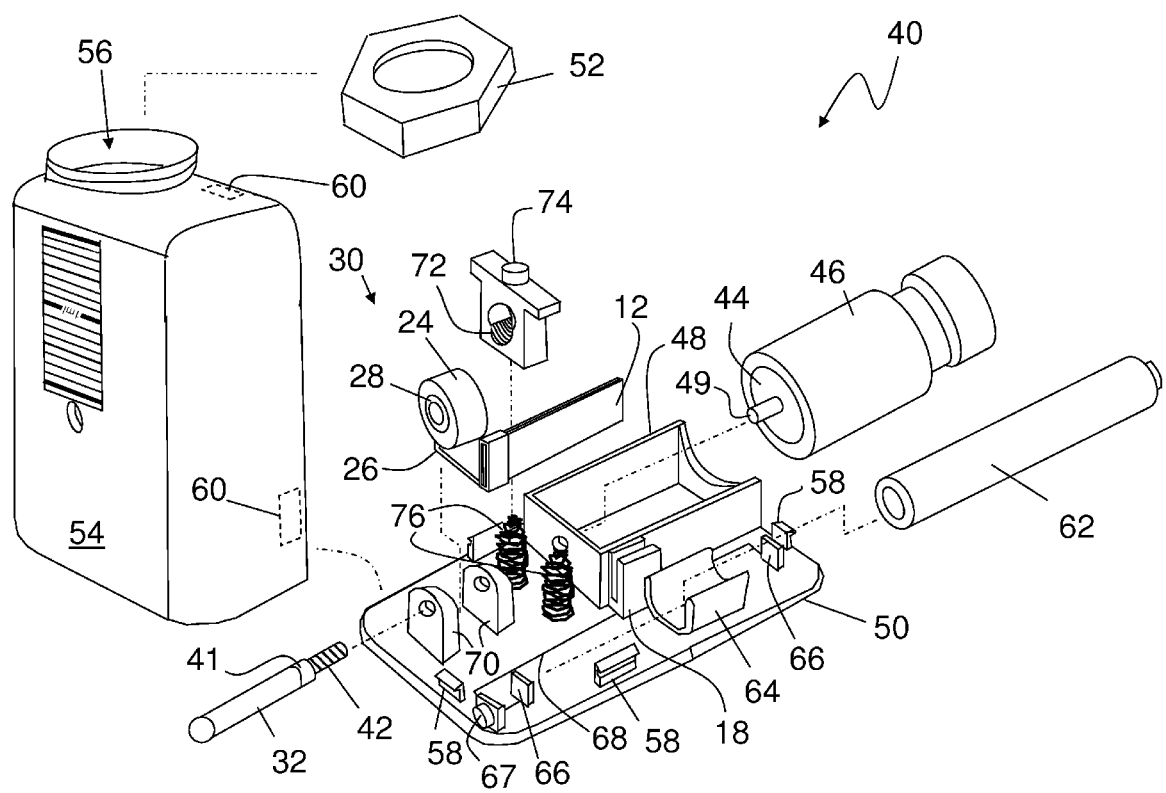
FIG. 4 is an exploded view of a miniature drug delivery pump embodiment shown with the piezoelectric drive system of FIG. 3.

With reference to FIG. 4, an exploded view of an embodiment of a miniature drug delivery pump, generally indicated by symbol 40 is shown, for example, with the piezoelectric drive system shown in FIG. 3. In all embodiments, the unidirectional rotational motion of the shaft 32 is used to advance a lead screw 42 from the cavity 33 of the shaft 32. In the illustrated embodiment shown by FIG. 4, a nut portion 41 is provided at the open end of the cavity 33 of the shaft 32. The threads (not shown) of the nut portion 41 engage the threads of the lead screw 42 and cause the movement of the lead screw 42 upon rotation of the shaft 32. Movement of the lead screw 42 advances a plunger or piston 44 to dispense a liquid drug from a drug container 46. As shown, the drug container 46 is accommodated in a cradle 48 of a base 50 of the delivery pump 40. In one embodiment, the lead screw 42 has a snap-in connection 49 to the piston 44 of the drug container 46.

In one embodiment, the drug container 46 is removable from the cradle 48 of the delivery pump 40, via removing a removable cap 52 from a cover 54 of the delivery pump 40 which permits removing and replacing the drug container 46 via an opening 56 defined in the cover 54. In such an embodiment, the opening 56 and/or the drug container 46 may be keyed or provided in shape which ensures proper alignment of the piston 44 with the lead screw 42. In another embodiment, the drug container 46 is not removable as the delivery pump 40 in such an embodiment is intended to be disposable after fully dispensing the liquid drug from the drug container 46.

In the illustrated embodiment of FIG. 4, the cover 54 snaps onto the base 50 without requiring separate cover fasteners via projections 58 of a pliable material which extend from the base 50 and resiliently seat into notches 60 provided in the inside surface of the cover 54. In an alternative embodiment, separate cover fasteners may be provided.

A battery 62 is also provided to power the drive system 30 of the delivery pump 40. The battery 62 in the illustrated embodiment is a size AAAA, which is about 42.5 mm long and about 8.3 mm in diameter, weighing around 6.5 grams. Output of alkaline batteries in this size is 1.5 volts, 625 mA·h. Although elements in the figures may be exaggerated in portion to other components, it is to be appreciated that the approximate relative size between the delivery pump 40 and the battery 62 is intended to be shown in the embodiment illustrated by FIG. 4. Accordingly, as shown the drug delivery pump 40 is not much larger than the AAAA battery 62, and is in one embodiment about 61 mm long, about 32 mm wide, and 15.5 mm in height, and weighs about 25 grams, with the drug container 46 holding 2 ml of a liquid drug. Such dimensions of the drug delivery pump 40 is about one fourth the size of existing conventional pumps. The small size and weight of the drug delivery pump 40 makes it easier for the patient to hold the delivery pump in place, such via an adhesive on the skin and/or to conceal the delivery pump under clothing.

The battery 62 is held in a battery cradle 64 provided in the base 50 and contacts electrical terminal posts 66. The wires 14 (FIGS. 1-3) of the piezoelectric drive system 30 each connect to a respective one of the posts 66 via an electrical circuit 68, for example, provided as a electrical trace in the base 50. In one embodiment, a switch or button 67 is also provided to the base 50, such that pushing down on the button 67 completes the electrical circuit 68 and energizes the piezoelectric bender 12 of the drive system 30. It is to be appreciated that other electrical components, such as a DC to AC inverter to produce a suitable drive voltage to the piezoelectric bender 12, and other control components are provided, but are not shown for convenience of illustration as the actual control and electrical system of the drug pump is not the focus of the present invention.

The shaft 32 which extends through and supports the wheel 24 and clutch 28 about the axis of rotation X, is supported in turn by a pair of base supports 70. In addition, and in one embodiment, the lead screw 42 extends through a keyhole 72 of a provided release button 74. A pair of springs 76 in this embodiment are also provided to the base 50, which bias a bottom portion 78 of the keyhole 72 against the lead screw 42. In this manner, threads 80 (best shown by FIG. 5) of the bottom portion 78 normally engage with the threads of the lead screw 42. Accordingly, in this embodiment where the drug container 46 is replaceable, pressing down on the release button 74 disengages the threads 80 with the threads of the lead screw 42 such that the lead screw 42 retracts back into the shaft 32 upon inserting a new drug cartridge into the delivery pump 40.

Figure 5:
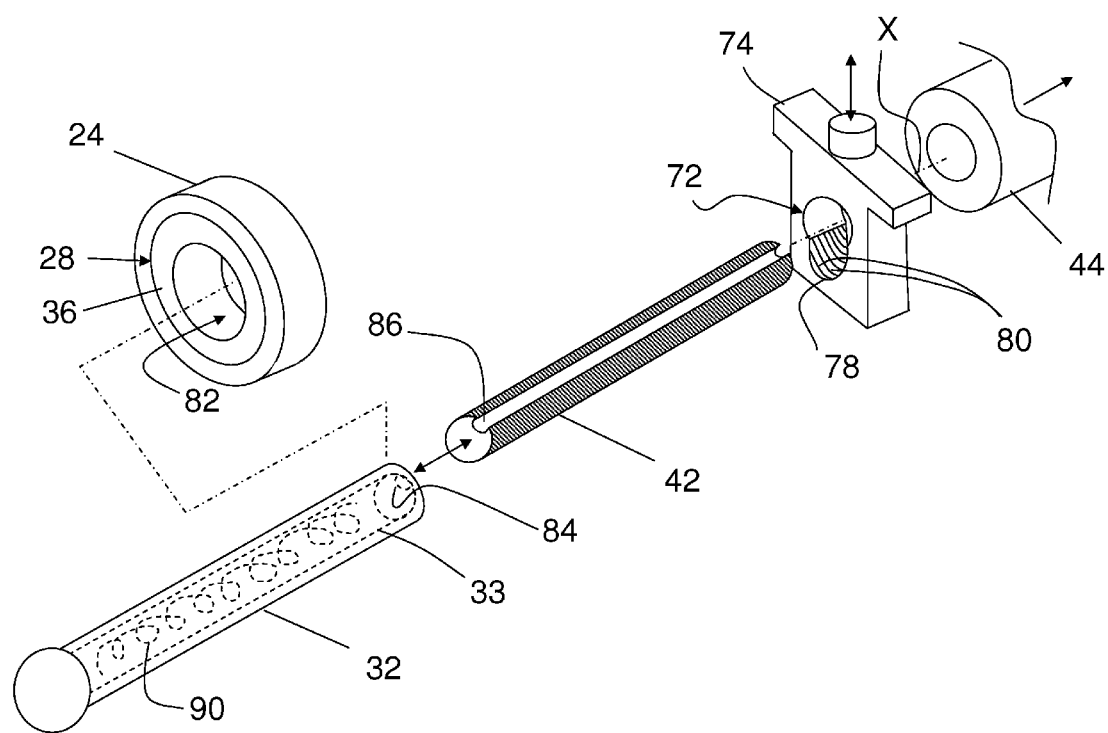
FIG. 5 is an exploded view of components of a piezoelectric drive system and their arrangement thereof according to the present invention.

With reference to FIG. 5, an exploded view of particular components of a piezoelectric drive system and their arrangement thereof according the above mentioned replaceable drug container embodiment of the present invention is shown. As in all the previous embodiments, the shaft 32 extends through a through bore 82 of the clutch body 36, and is rotatable mounted therein to rotate only unidirectionally with the clutch 28. In this embodiment, the lead screw 42 is slidably accommodated in the cavity 33 of the shaft 32, wherein the nut portion 41 (FIG. 4) of the previous non-replaceable drug cartridge embodiment is not provided A detent portion 84 of the shaft 32 is provided inside the cavity 33 and rides in a longitudinally extending flat or slot 86 provided in the lead screw 42. In this manner, the lead screw 42 will rotate only in sync with the shaft 32, when the shaft 32 is rotated by the clutch 28. However, as the shaft 32 is rotated, the lead screw 42 both rotates and advances slidably out of the cavity 33 along the rotational axis X. As the mentioned above previously, movement of the lead screw 42 (i.e., translational along the rotational axis X) advances the piston 44 to dispense a liquid drug from the drug container 46. In one embodiment, the detent portion 84 is provided as a round bearing end to minimize friction due to the inherent thrust loads encountered in operation of the lead screw 42 pushing the piston 44 forward.

Optionally, a biasing member 90, such as a spring, may be provided in the cavity 33 to ensure contact of the lead screw 42 with the piston 44. The biasing member 90, however, provides a relatively weak pushing force which is less than the pushing force needed to move the piston 44 in order to dispense the liquid drug from the drug container 46 (FIG. 5).

Table 1 below discloses the pushing force generated by two illustrated drive systems embodiments according to the present invention which is applied to the piston 44.

TABLE 1

| | | Force Generation | | |
|---|---|---|---|---|
| Test No. | Bender Free length | Drive Voltage | Lead Screw | Force |
| #1 | 1.0 inch (25.4 mm) | +/−170 DC Sine wave | .282 mm pitch SS 1.15 mm OD | 9 Newton (stall) |
| #2 | 1.0 inch (25.4 mm) | +/−170 DC Sine wave | 0.453 mm pitch SS 1.87 mm OD | 24.3 Newton (near stall) |

Figure 6:
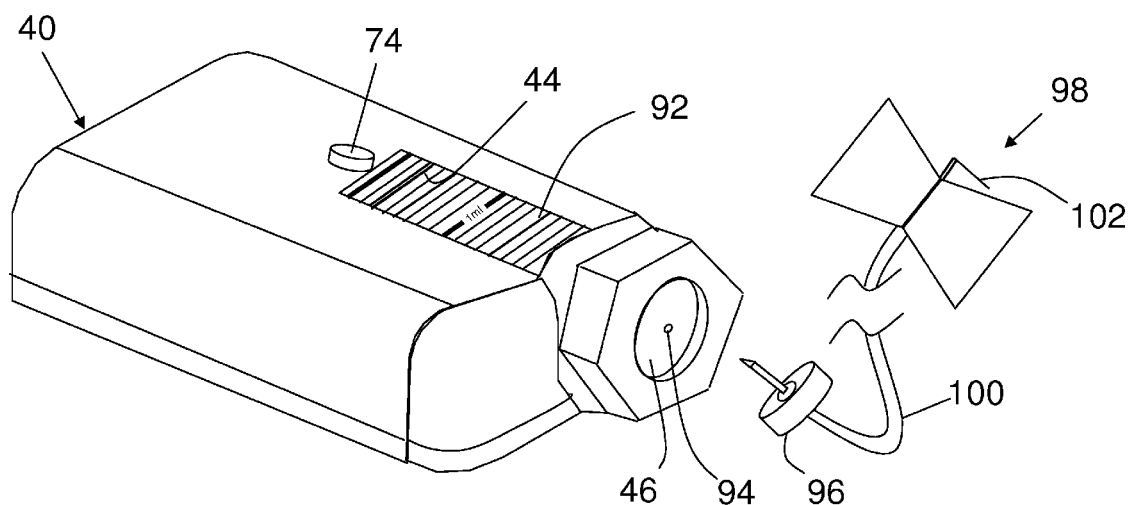
FIG. 6 is a perspective view of the miniature drug delivery pump embodiment of FIG. 4 according to the present invention.

As shown by FIG. 6, the drug delivery pump 40 provides a scaled window 92 through which a portion of piston 44 is visible and by which the patient in one embodiment uses to determine the amount of drug remaining in the cartridge so that they don't inadvertently run out at an inconvenient time. In another embodiment, dispensing of very small amounts of the liquid drug can be provided by controlling the drive system with a timed switching circuit, wherein depressing button 72 activates the timed switching circuit which energizes the drive system for a predetermined period per button push. In another embodiment, a programmable constant rate or basal rate delivery with a manual override (for bolus delivery) may also be provided. The drug container 46 includes an injection site 94 which is used to connect a spike or other suitable type of connector 96 of an administration set 98 to the delivery pump 40. The spike or other suitable type of connector 96 is connected to a fluid conduit 100 which at the distal end connects to a catheter 102, which enters the patient's intravenous system through the skin for delivery of the liquid drug.

Although not limited to, some of the noted advantages of the present invention are as follows: the inherent precision of the motion from the piezoelectric bender which can be used to accurately deliver very small doses (i.e., about 0.003 ml), the ability to run at high frequency (up to 100 hz) to deliver quickly a large dose (i.e., 0.1 ml), nearly silent operation, fewer moving parts, and inexpensive parts. Such advantages result in an overall compact and low cost drug delivery pump for the consumer.

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art.

What is claimed is:

1. A drive system comprising:
   a lead screw having a rotational axis;
   a shaft extending along the rotational axis and configured to rotate the lead screw about the rotational axis;
   a piezoelectric bender configured to produce reciprocating lateral motion adjacent the rotational axis; and
   a clutch coupled to the shaft and configured to rotate about the rotational axis and operably connected to the piezoelectric bender, wherein the clutch is arranged to convert the reciprocating lateral motion of the piezoelectric bender into reciprocating rotary motion about the rotational axis, and wherein the clutch in only one direction turns the shaft which advances the lead screw.

2. The drive system according to claim 1, wherein the shaft has a nut portion which engages threads of the lead screw.

3. The drive system according to claim 1, wherein the shaft provides a cavity into which the lead screw is slidably accommodated.

4. The drive system according to claim 1, wherein the shaft provides a cavity into which the lead screw is slidably accommodated, and has a mating nut portion at the open end to provided advancement of the lead screw.

5. The drive system according to claim 1, wherein the shaft provides a cavity into which the lead screw is slidably accommodated, and has a detent or shaped portion acting as a key-way connection provided inside the cavity which rides in a longitudinally extending slot provided in the lead screw, and said drive system further comprises a release button having threads arranged to engage under spring tension with the lead screw such that as the shaft is rotated the lead screw advances slidably out of the cavity, and to disengage the threads with the lead screw when the release button is pushed.

6. The drive system according to claim 1 wherein the shaft provides a cavity into which the lead screw is slidably accommodated, and a biasing member provided in the cavity and configured to urge the lead screw from the cavity.

7. The drive system according to claim 1 wherein the piezoelectric bender extends longitudinally perpendicular to the rotational axis and is connected directly to a wheel mounted to the clutch.

8. The drive system according to claim 7 wherein the piezoelectric bender extends longitudinally parallel to the rotational axis and is connected to the wheel via an extension having a first portion surrounding an end of the piezoelectric bender and a second portion provided a distance from the first portion which is coupled to the wheel.

9. The drive system according to claim 7 wherein the piezoelectric bender extends longitudinally parallel to the rotational axis and is connected to the wheel via a wire wrapped at least partially around the wheel, wherein the wire is tensioned around the wheel via a spring.

10. The drive system according to claim 1 wherein the piezoelectric bender comprises a bi-morph piezoelectric crystal structure.

11. The drive system according to claim 10 wherein the bi-morph piezoelectric crystal structure is a laminate piezoelectric crystal stack.

12. The drive system according to claim 1 further comprising a battery to power the drive system.

13. The drive system according to claim 1 provided in a drug delivery pump having a drug container, wherein the lead screw has a snap-in connection to a piston of the drug container.

14. The drive system according to claim 1 provided in a drug delivery pump having a drug container, wherein the lead screw has a snap-in connection to a piston of the drug container, and the drug delivery pump is about 61 mm long, about 32 mm wide, and 15.5 mm in height, and the drug container holds 2 ml of a liquid drug.

15. The drive system according to claim 5 provided in a drug delivery pump having a drug container, wherein the lead screw has a snap-in connection to a piston of the drug container, and wherein the detent or shaped portion has a round bearing end to minimize friction due to the inherent thrust loads encountered in operation of the lead screw pushing the piston forward.

16. A method for dispensing a liquid drug from a drug container having a piston, said method comprising:
    providing a lead screw connected to the piston of the drug container, the lead screw having a rotational axis;
    providing a shaft extending along the rotational axis and configured to rotate the lead screw about the rotational axis;
    providing a piezoelectric bender configured to produce reciprocating lateral motion adjacent the rotational axis;
    providing a clutch coupled to the shaft and configured to rotate about the rotational axis; and
    providing a wheel mounted to the clutch and operably connected to the piezoelectric bender, wherein the wheel converts the reciprocating lateral motion of the piezoelectric bender into reciprocating rotary motion about the rotational axis turning the clutch bi-directionally, and wherein the clutch in only one direction turns the shaft which advances the lead screw and the piston dispensing the liquid drug from the drug container.

17. The method according to claim 16 further comprises activating the piezoelectric bender which turns the lead screw in the one direction and advances the piston to dispense the liquid drug from the drug container.

18. The method according to claim 16 further comprises provided the piezoelectric bender to extend longitudinally perpendicular to the rotational axis and connecting the piezoelectric bender directly to the wheel.

19. The method according to claim 16 further comprises providing the piezoelectric bender to extend longitudinally parallel to the rotational axis and connecting the piezoelectric bender to the wheel via an extension or wire.

20. The method according to claim 16 wherein the piezoelectric bender extends longitudinally perpendicular to the rotational axis and is connected directly to the wheel, and the method further comprises activating the piezoelectric bender which turns the lead screw in the one direction and advances the piston to dispense the liquid drug from the drug container.

21. The method according to claim 16 wherein the piezoelectric bender extends longitudinally parallel to the rotational axis and is connected to the wheel via an extension, and the method further comprises activating the piezoelectric bender which turns the lead screw in the one direction and advances the piston to dispense the liquid drug from the drug container.

* * * * *